United States Patent
Mikami et al.

(10) Patent No.: US 9,810,674 B2
(45) Date of Patent: Nov. 7, 2017

(54) METHOD FOR EVALUATING FOOD PREFERENCE OF PETS

(71) Applicant: AJINOMOTO CO., INC., Chuo-ku (JP)

(72) Inventors: Takashi Mikami, Kawasaki (JP); Chinatsu Kasamatsu, Kawasaki (JP); Eisuke Higuchi, Kawasaki (JP); Takeshi Fujieda, Kawasaki (JP)

(73) Assignee: Ajinomoto Co., Inc., Chuo-ku (JP)

( * ) Notice: Subject to any disclaimer, the term of this patent is extended or adjusted under 35 U.S.C. 154(b) by 0 days.

(21) Appl. No.: 14/230,606

(22) Filed: Mar. 31, 2014

(65) Prior Publication Data

US 2014/0295037 A1  Oct. 2, 2014

(30) Foreign Application Priority Data

Mar. 29, 2013 (JP) ................................. 2013-071564

(51) Int. Cl.
| | |
|---|---|
| *G01N 33/02* | (2006.01) |
| *A23K 40/00* | (2016.01) |
| *A23K 20/10* | (2016.01) |
| *A23K 50/40* | (2016.01) |

(52) U.S. Cl.
CPC ............. *G01N 33/02* (2013.01); *A23K 20/10* (2016.05); *A23K 40/00* (2016.05); *A23K 50/40* (2016.05)

(58) Field of Classification Search
None
See application file for complete search history.

(56) References Cited

U.S. PATENT DOCUMENTS

| | | | |
|---|---|---|---|
| 2008/0193591 A1* | 8/2008 | Wada | A23L 27/45 426/7 |
| 2012/0021094 A1* | 1/2012 | Sunvold | A23K 1/1853 426/61 |
| 2013/0287930 A1* | 10/2013 | Bramoulle et al. | 426/656 |

OTHER PUBLICATIONS

Benoit Rousseau, Daniel M. Ennis, Frank Rossi, Internal preference mapping and the issue of satiety, Sep. 29, 2011, Food Quality and Preference, vol. 24, p. 67-74.*
Jean-Francois Meullenet, Rui Xiong, Christopher J Findlay, Multidimensional Scaling and Unfolding and the Application of Probabilistic Unfolding to Model Preference Data in Multivariate and Probabilistic Analyses of Sensory Science Problems, 2007, Blackwell Publishing, pp. 95-110.*
G. J. Pickering, Optimizing the sensory characteristics and acceptance of canned cat food: use of a human taste panel, Feb. 27, 2008, Journal of Animal Physiology and Animal Nutrition, vol. 93, p. 52-60.*

(Continued)

*Primary Examiner* — John S Brusca
*Assistant Examiner* — Olivia Wise
(74) *Attorney, Agent, or Firm* — Oblon, McClelland, Maier & Neustadt, L.L.P.

(57) ABSTRACT

A method, a program, and a device for evaluating food preference of pets that do not require humans to eat a pet food itself. The preference of pets can be evaluated by conducting sensory analysis on selected palatants contained in a pet food by humans. Accordingly, highly precise prediction of the preference can be made by a simple and intuitive method based on sensory attributes for human. Further, humans are not required to eat a pet food itself because the humans may conduct sensory analysis on selected palatants contained in the pet food.

12 Claims, 23 Drawing Sheets

(56) References Cited

OTHER PUBLICATIONS

B. Di Donfrancesco, K. Koppel, E. Chambers IV. An Initial Lexicon for Sensory Properties of Dry Dog Food, Dec. 2012, Journal of Sensory Studies, vol. 27, p. 498-510.*

Fay Ferrell, Effects of Restricted Dietary Flavor Experience Before Weaning on Postweaning Food Preference in Puppies, 1984, Neuroscience & Biobehavioral Reviews, vol. 8, p. 191-198.*

AFB International. Principles of Pet Food Palatability. Aug. 22, 2013. p. 1-5.*

Nancy Kerns. Pet Food Companies and Animal Research: What Do They Do? The Whole Dog Journal, Jun. 2012, p. 1-13.*

D Jayasena, DU Ahn, KC Nam, C Jo. Flavour Chemistry of Chicken Meat: A Review. Asian Australas. J. Anim. Sci. May 2013, vol. 26, No. 5, p. 732-742.*

H Kawasaki, A Yamada, R Fuse, T Fushiki. Preference for Dried Bonito Broth in Olfactory-Blocked or Taste Nerve-Sectioned Mice in the Two-Bottle Choice Test. Bioscience, Biotechnology, and Biochemistry. 2008, vol. 72, No. 11, p. 2840-2846.*

ASTM Internationl. Standard Terminology Relating to Sensory Evaluation of Materials and Products. Dec. 2012, p. 1-6.*

HN Lioe, J Selamat, M Yasuda. Soy Sauce and Its Umami Taste: A link from the Past to Current Situation. Journal of Food Science. 2010, vol. 75, No. 3, p. R71-R76.*

VK Pasupuleti, C Holmes, AL Demain. "Applications of Protein Hydrolysates in Biotechnology", Chapter 1, Protein Hydrolysates in Biotechnology. VK Pasupuleti, AL Demain, ed. 2010, Springer.*

B. Di Donfrancesco et al, "An Initial Lexicon for Sensory Properties of Dry Dog Food", Journal of Sensory Studies, 27 (2012) pp. 498-510.

* cited by examiner

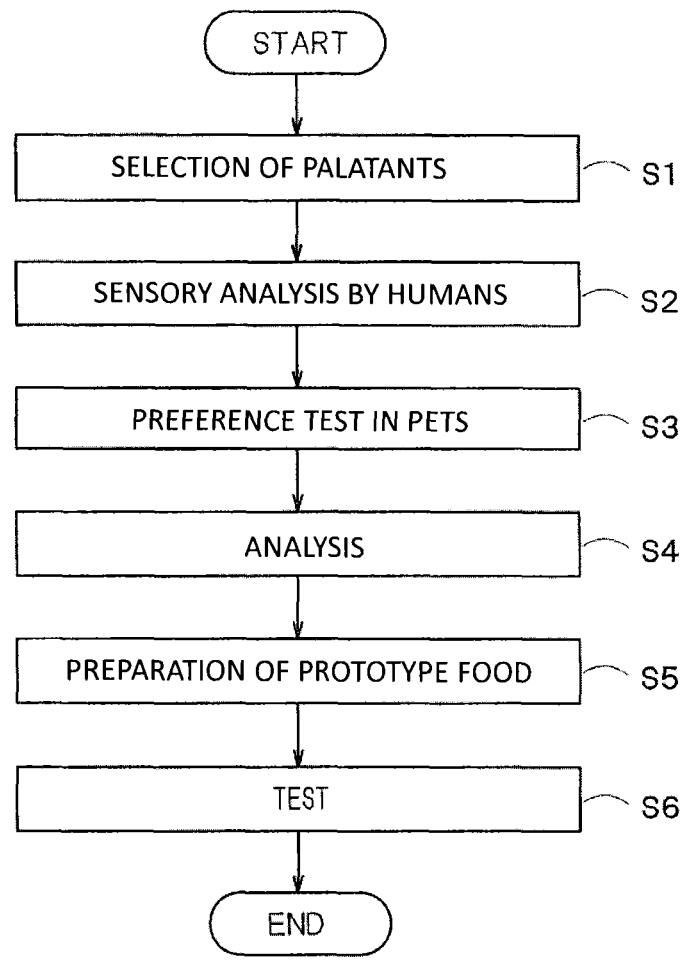
F I G. 1

| PALATANT | FEATURE OF PALATANT |
|---|---|
| ROAST FLAVOR TYPE HYDROLYZED SOYBEAN PROTEIN (HYDROLYZED SOYBEAN PROTEIN (ROAST)) | MATERIAL HAVING A STEWED BEEF-FLAVOR THAT IS OBTAINED BY HEATING A FILTRATE OF SOYBEAN HYDROLYSATE AND SUGAR |
| BEER YEAST EXTRACT | MATERIAL OBTAINED BY ENZYME TREATMENT OF DRIED BEER YEAST |
| MEAT-LIKE FLAVOR MATERIAL | MATERIAL HAVING A MEAT-LIKE FLAVOR CONTAINING METHIONAL THAT IS OBTAINED UTILIZING A REACTION BETWEEN METHIONINE AND SUGAR BY HEATING |
| HYDROLYZED SOYBEAN PROTEIN | MATERIAL THAT IS OBTAINED BY DESALTING A FILTRATE OF SOYBEAN HYDROLYSATE BY AN ION EXCHANGE RESIN |
| TORULA YEAST EXTRACT | YEAST EXTRACT HAVING HIGH GLUTATHIONE CONTENT |
| BEEF EXTRACT | MATERIAL OBTAINED BY HEATING BEEF EXTRACT |
| DRIED BONITO EXTRACT | SEASONING HAVING "SMELL AND FLAVOR" OF DRIED BONITO |
| CHEESE FOOD (CHEESE PASTE) | PASTE MATERIAL THAT IS OBTAINED BY CONCENTRATING IN GOOD BALANCE OF AROMA AND FLAVOR SPECIFIC TO NATURAL CHEESE |

FIG. 2

| | |
|---|---|
| SENSORY ATTRIBUTES INDICATING TASTE | SOUR TASTE |
| | BITTER TASTE |
| | SALTY TASTE |
| | SWEET TASTE |
| | UMAMI TASTE |
| | MILDNESS |
| | TASTE INTENSITY |
| | TASTE PERSISTENCE |
| SENSORY ATTRIBUTES INDICATING AROMA | SOUR AROMA |
| | FERMENTATION AROMA |
| | ROAST AROMA |
| | SWEET AROMA |
| | FISHY AROMA |
| | SULFUROUS AROMA |
| SENSORY ATTRIBUTES INDICATING FLAVOR | SOY SAUCE-ROASTED FLAVOR |
| | OCEAN AND DRIED FISH FLAVOR |
| | ANIMAL-LIKE FLAVOR |
| | SOUR FLAVOR |

FIG. 3

| SENSORY ATTRIBUTES | | HYDROLYZED SOYBEAN PROTEIN (ROAST) | BEER YEAST EXTRACT | TORULA YEAST EXTRACT | MEAT-LIKE FLAVOR MATERIAL | BEEF EXTRACT | CHEESE FOOD | DRIED BONITO EXTRACT |
|---|---|---|---|---|---|---|---|---|
| TASTE | SOUR TASTE | 4 | 3 | 1 | 1 | 1 | 4 | 1.5 | 1.2 |
| | BITTER TASTE | 1.5 | 1.5 | 4 | 1 | 1 | 3.5 | 1 | 3 |
| | SALTY TASTE | 4 | 1.5 | 2 | 1 | 2.5 | 2.5 | 1 | 1.5 |
| | SWEET TASTE | 1 | 1.5 | 2 | 1 | 2.5 | 1 | 1.5 | 1.2 |
| | UMAMI TASTE | 2 | 3 | 1.5 | 2 | 1.5 | 2.5 | 1.5 | 1 |
| | MILDNESS | 1 | 1 | 1 | 4 | 3 | 2 | 2 | 1.5 |
| | TASTE INTENSITY | 4 | 3 | 2.5 | 1.5 | 2.5 | 4 | 1.5 | 2 |
| | TASTE PERSISTENCE | 1.5 | 2 | 4 | 4 | 2 | 4 | 2.5 | 2 |
| AROMA | SOUR AROMA | 3.5 | 3 | 1 | 1 | 1.5 | 3 | 4.5 | 1.5 |
| | FERMENTATION AROMA | 1 | 1 | 3.5 | 1 | 1 | 2 | 4.5 | 1 |
| | ROAST AROMA | 4 | 1.5 | 1 | 1 | 1 | 2 | 1 | 3 |
| | SWEET AROMA | 1 | 1 | 3 | 2.5 | 1 | 2.5 | 1.5 | 1 |
| | FISHY AROMA | 1 | 1 | 1 | 1 | 1 | 5 | 3 | 1 |
| | SULFUROUS AROMA | 1 | 1 | 1 | 4 | 3 | 1 | 2 | 1 |
| FLAVOR | SOY SAUCE-ROASTED FLAVOR | 4 | 2 | 2.5 | 1 | 1 | 4.5 | 1 | 2 |
| | OCEAN AND DRIED FISH FLAVOR | 1 | 1 | 1 | 1 | 2 | 1 | 1 | 3 |
| | ANIMAL-LIKE FLAVOR | 1 | 1 | 1 | 1.5 | 1 | 5 | 1 | 1 |
| | SOUR FLAVOR | 4 | 3 | 1.5 | 1.5 | 1 | 5 | 2 | 1.5 |

FIG. 4

(a) BEAGLE

| No | AGE | SEX |
|----|-----|-----|
| 1  | 2   | M   |
| 2  | 2   | XM  |
| 3  | 2   | XM  |
| 4  | 2   | F   |
| 5  | 3   | M   |
| 6  | 5   | M   |
| 7  | 5   | M   |
| 8  | 7   | F   |
| 9  | 7   | F   |
| 10 | 7   | F   |

| No | AGE | SEX |
|----|-----|-----|
| 11 | 8   | F   |
| 12 | 8   | F   |
| 13 | 9   | M   |
| 14 | 9   | XM  |
| 15 | 9   | F   |
| 16 | 9   | F   |
| 17 | 10  | F   |
| 18 | 12  | XF  |

M: MALE
F: FEMALE
XM: CASTRATED MALE
XF: SPAYED FEMALE (b) SMALL BREED DOGS

| No | AGE | SEX | BREED TYPE  |
|----|-----|-----|-------------|
| 1  | 9   | M   | SHIH-TZU    |
| 2  | 4   | M   | CHIHUAHUA   |
| 3  | 4   | M   | TOY POODLE  |
| 4  | 8   | M   | CHIHUAHUA   |
| 5  | 8   | M   | POMERANIAN  |
| 6  | 3   | M   | M DACHSHUND |
| 7  | 1   | M   | M DACHSHUND |
| 8  | 6   | F   | M DACHSHUND |
| 9  | 8   | F   | POMERANIAN  |
| 10 | 6   | F   | M DACHSHUND |

| No | AGE | SEX | BREED TYPE       |
|----|-----|-----|------------------|
| 11 | 10  | XF  | CHIHUAHUA        |
| 12 | 8   | F   | SHIH-TZU         |
| 13 | 2   | F   | TOY POODLE       |
| 14 | 4   | F   | TOY POODLE       |
| 15 | 3   | M   | YORKSHIRE TERRIER|
| 16 | 1   | M   | TOY POODLE       |
| 17 | 1   | F   | TOY POODLE       |
| 18 | 1   | M   | TOY POODLE       |
| 19 | 3   | F   | YORKSHIRE TERRIER|

| | HYDROLYZED SOYBEAN PROTEIN (ROAST) | BEER YEAST EXTRACT | MEAT-LIKE FLAVOR MATERIAL | SOYBEAN PROTEIN HYDROLYSATE | TORULA YEAST EXTRACT | BEEF EXTRACT | DRIED BONITO EXTRACT | CHEESE FOOD |
|---|---|---|---|---|---|---|---|---|
| 1 | 6 | 11 | 9 | 11 | 4 | 11 | 8 | 11 |
| 2 | 11 | 10 | 10 | 11 | 7 | 10 | 10 | 9 |
| 3 | 11 | 11 | 11 | 11 | 11 | 11 | 10 | 11 |
| 4 | 1 | 6 | 5 | 9 | 8 | 5 | 6 | 6 |
| 5 | 10 | 9 | 8 | 11 | 10 | 3 | 11 | 8 |
| 6 | 2 | 4 | 6 | 1 | 3 | 2 | 4 | 10 |
| 7 | 11 | 7 | 11 | 9 | 11 | 11 | 2 | 11 |
| 8 | 1 | 5 | 11 | 2 | 10 | 6 | 9 | 10 |
| 9 | 11 | 11 | 10 | 9 | 11 | 11 | 11 | 11 |
| 10 | 8 | 8 | 7 | 11 | 10 | 10 | 10 | 11 |
| 11 | 11 | 9 | 6 | 8 | 11 | 8 | 10 | 11 |
| 12 | 7 | 5 | 7 | 11 | 10 | 8 | 5 | 11 |
| 13 | 8 | 6 | 10 | 4 | 7 | 7 | 9 | 11 |
| 14 | 9 | 8 | 11 | 11 | 8 | 11 | 8 | 11 |
| 15 | 6 | 7 | 10 | 10 | 10 | 6 | 6 | 11 |
| 16 | 8 | 9 | 6 | 11 | 10 | 10 | 8 | 10 |
| 17 | 11 | 9 | 9 | 10 | 10 | 8 | 11 | 10 |
| 18 | 6 | 6 | 11 | 8 | 6 | 11 | 7 | 11 |
| AVERAGE | 7.67 | 7.72 | 8.78 | 8.78 | 8.72 | 8.28 | 8.06 | 10.22 |
| STANDARD DEVIATION | 3.48 | 2.24 | 2.10 | 3.19 | 2.44 | 2.91 | 2.60 | 1.35 |

FIG. 7

| | HYDROLYZED SOYBEAN PROTEIN (ROAST) | BEER YEAST EXTRACT | MEAT-LIKE FLAVOR MATERIAL | SOYBEAN PROTEIN HYDROLYSATE | TORULA YEAST EXTRACT | BEEF EXTRACT | DRIED BONITO EXTRACT | CHEESE FOOD |
|---|---|---|---|---|---|---|---|---|
| 1 | 11 | 11 | 6 | 10 | 9 | 11 | 11 | 11 |
| 2 | 11 | 9 | 9 | 10 | 9 | 11 | 9 | 11 |
| 3 | 11 | 9 | 10 | 4 | 5 | 9 | 6 | 8 |
| 4 | 11 | 11 | 11 | 11 | 11 | 6 | 1 | 11 |
| 5 | 3 | 11 | 6 | 9 | 10 | 11 | 2 | 11 |
| 6 | 11 | 7 | 7 | 10 | 4 | 10 | 10 | 10 |
| 7 | 11 | 3 | 11 | 11 | 7 | 1 | 11 | 11 |
| 8 | 11 | 10 | 11 | 5 | 5 | 11 | 11 | 11 |
| 9 | 9 | 10 | 10 | 9 | 6 | 10 | 8 | 11 |
| 10 | 10 | 8 | 8 | 8 | 7 | 11 | 8 | 11 |
| 11 | 10 | 9 | 9 | 11 | 7 | 9 | 8 | 11 |
| 12 | 10 | 9 | 7 | 9 | 10 | 8 | 5 | 9 |
| 13 | 10 | 11 | 8 | 10 | 7 | 11 | 8 | 11 |
| 14 | 11 | 11 | 6 | 10 | 6 | 6 | 8 | 11 |
| 15 | 10 | 9 | 6 | 8 | 7 | 8 | 7 | 11 |
| 16 | 10 | 11 | 6 | 11 | 11 | 11 | 7 | 10 |
| 17 | 11 | 11 | 6 | 10 | 11 | 5 | 9 | 10 |
| 18 | 11 | 11 | 5 | 10 | 11 | 7 | 9 | 9 |
| 19 | 11 | 10 | 7 | 11 | 10 | 11 | 6 | 11 |
| AVERAGE | 10.16 | 9.53 | 7.84 | 9.32 | 8.11 | 8.79 | 7.58 | 10.47 |
| STANDARD DEVIATION | 1.83 | 1.98 | 2.01 | 1.95 | 2.38 | 2.76 | 2.73 | 0.90 |

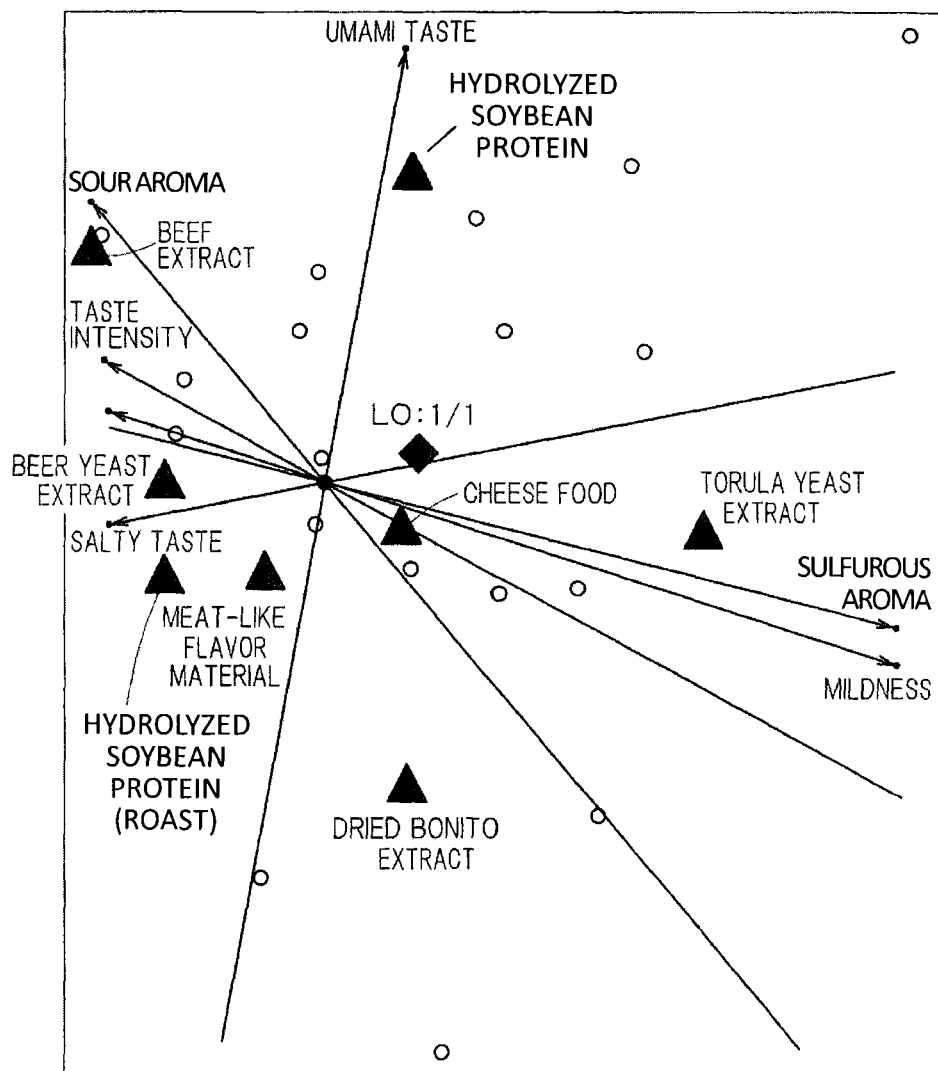
F I G. 8

| SENSORY ATTRIBUTES | | CORRELATION COEFFICIENT |
|---|---|---|
| TASTE | SOUR TASTE | 0.709 |
| | BITTER TASTE | 0.674 |
| | SALTY TASTE | 0.764 |
| | SWEET TASTE | 0.450 |
| | UMAMI TASTE | 0.932 |
| | MILDNESS | 0.831 |
| | TASTE INTENSITY | 0.849 |
| | TASTE PERSISTENCE | 0.290 |
| AROMA | SOUR AROMA | 0.402 |
| | FERMENTATION AROMA | 0.261 |
| | ROAST AROMA | 0.679 |
| | SWEET AROMA | 0.273 |
| | FISHY AROMA | 0.697 |
| | SULFUROUS AROMA | 0.835 |
| FLAVOR | SOY SAUCE-ROASTED FLAVOR | 0.830 |
| | OCEAN AND DRIED FISH FLAVOR | 0.686 |
| | ANIMAL-LIKE FLAVOR | 0.686 |
| | SOUR FLAVOR | 0.719 |

F I G. 9

| CONTRIBUTING ATTRIBUTE | CORRELATION COEFFICIENT | PREDICTED OPTIMAL SCORE |
|---|---|---|
| SOUR TASTE | 0.709 | 1.88 |
| SALTY TASTE | 0.764 | 1.56 |
| UMAMI TASTE | 0.932 | 2.04 |
| MILDNESS | 0.831 | 2.42 |
| TASTE INTENSITY | 0.849 | 2.32 |
| SULFUROUS AROMA | 0.835 | 2.27 |
| SOY SAUCE/ROASTED | 0.830 | 1.70 |
| SOUR FLAVOR | 0.719 | 2.26 |

FIG. 10

| CONTRIBUTING ATTRIBUTE | CORRELATION COEFFICIENT | PREDICTED OPTIMAL SCORE |
|---|---|---|
| BITTER TASTE | 0.789 | 2.34 |
| SWEET TASTE | 0.791 | 1.43 |
| TASTE PERSISTENCE | 0.875 | 2.99 |
| SWEET AROMA | 0.870 | 1.79 |
| FISHY AROMA | 0.845 | 2.12 |
| OCEAN AND DRIED FISH FLAVOR | 0.866 | 1.38 |
| ANIMAL-LIKE FLAVOR | 0.851 | 1.86 |

FIG. 12

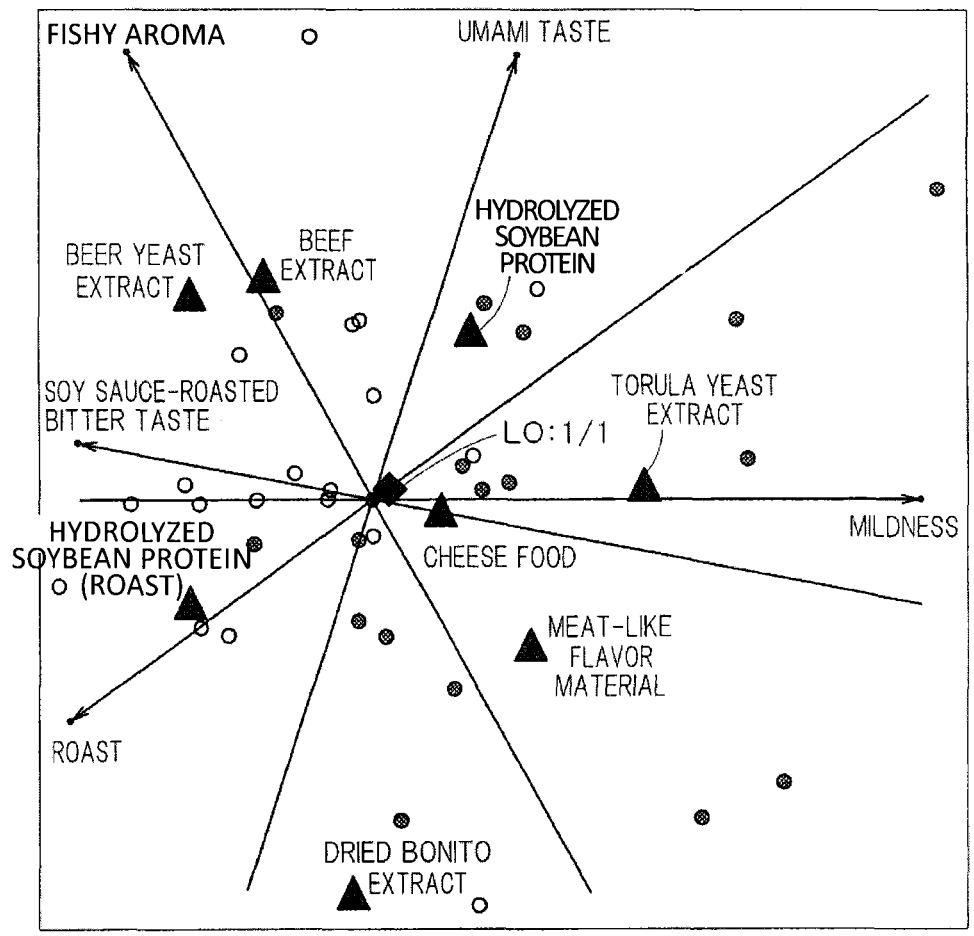
F I G. 13

| CONTRIBUTING ATTRIBUTE | CORRELATION COEFFICIENT | PREDICTED OPTIMAL SCORE |
|---|---|---|
| BITTER TASTE | 0.721 | 2.05 |
| UMAMI TASTE | 0.720 | 1.90 |
| MILDNESS | 0.812 | 1.99 |
| ROAST AROMA | 0.812 | 1.71 |
| FISHY AROMA | 0.717 | 1.90 |
| SULFUROUS AROMA | 0.836 | 1.79 |
| SOY SAUCE/ROASTED | 0.817 | 2.25 |
| OCEAN AND DRIED FISH FLAVOR | 0.854 | 1.35 |

FIG. 14

| PROTO TYPE FOOD | PALATANT 1 | PALATANT 2 | PALATANT 3 | BLENDING RATIO |
|---|---|---|---|---|
| A | DRIED BONITO EXTRACT | HYDROLYZED SOYBEAN PROTEIN | TORULA YEAST EXTRACT | 2:2:1 |
| B | BEEF EXTRACT | MEAT-LIKE MATERIAL | HYDROLYZED SOYBEAN PROTEIN | 2:2:1 |
| C | CHEESE FOOD | MEAT-LIKE MATERIAL | HYDROLYZED SOYBEAN PROTEIN | 10:3:7 |
| D | HYDROLYZED SOYBEAN PROTEIN (ROAST) | BEER YEAST EXTRACT | MEAT-LIKE MATERIAL | 1:1:1 |

| SENSORY ATTRIBUTES | | BEAGLE | PROTOTYPE FOOD A | PROTOTYPE FOOD B | PROTOTYPE FOOD C | PROTOTYPE FOOD D |
|---|---|---|---|---|---|---|
| TASTE | SOUR TASTE | 1.88 | 2 | 2.3 | 2.2 | 2.1 |
| | BITTER TASTE | 1.57 | 2 | 2.1 | 1.9 | 2 |
| | SALTY TASTE | 1.56 | 1 | 2 | 1.4 | 2.8 |
| | SWEET TASTE | 1.47 | 1.5 | 1.9 | 1.4 | 1.9 |
| | UMAMI TASTE | 2.04 | 1.6 | 2.2 | 1.9 | 1.9 |
| | MILDNESS | 2.42 | 2 | 1.8 | 2.3 | 2.5 |
| | TASTE INTENSITY | 2.32 | 1.8 | 2.9 | 2.3 | 2.3 |
| | TASTE PERSISTENCE | 2.88 | 2 | 2.5 | 2.2 | 3.1 |
| AROMA | SOUR AROMA | 2.44 | 1.5 | 2.4 | 4.5 | 2 |
| | FERMENTATION AROMA | 1.85 | 1 | 1.3 | 4.3 | 1.6 |
| | ROAST AROMA | 1.31 | 1.8 | 1.5 | 1.2 | 1.3 |
| | SWEET AROMA | 1.70 | 1.3 | 1.2 | 1 | 1.3 |
| | FISHY AROMA | 1.91 | 1.4 | 1.8 | 2 | 1 |
| | SULFUROUS ODOR | 2.27 | 1.6 | 1.4 | 2 | 1.6 |
| | SOY SAUCE-ROASTED FLAVOR | 1.70 | 1.5 | 2 | 1.4 | 2.3 |
| FLAVOR | OCEAN AND DRIED FISH FLAVOR | 1.27 | 2 | 1.2 | 1.2 | 1.3 |
| | ANIMAL-LIKE FLAVOR | 1.52 | 1.1 | 1.3 | 1.1 | 1 |
| | SOUR FLAVOR | 2.26 | 1.8 | 2.8 | 2.6 | 2 |

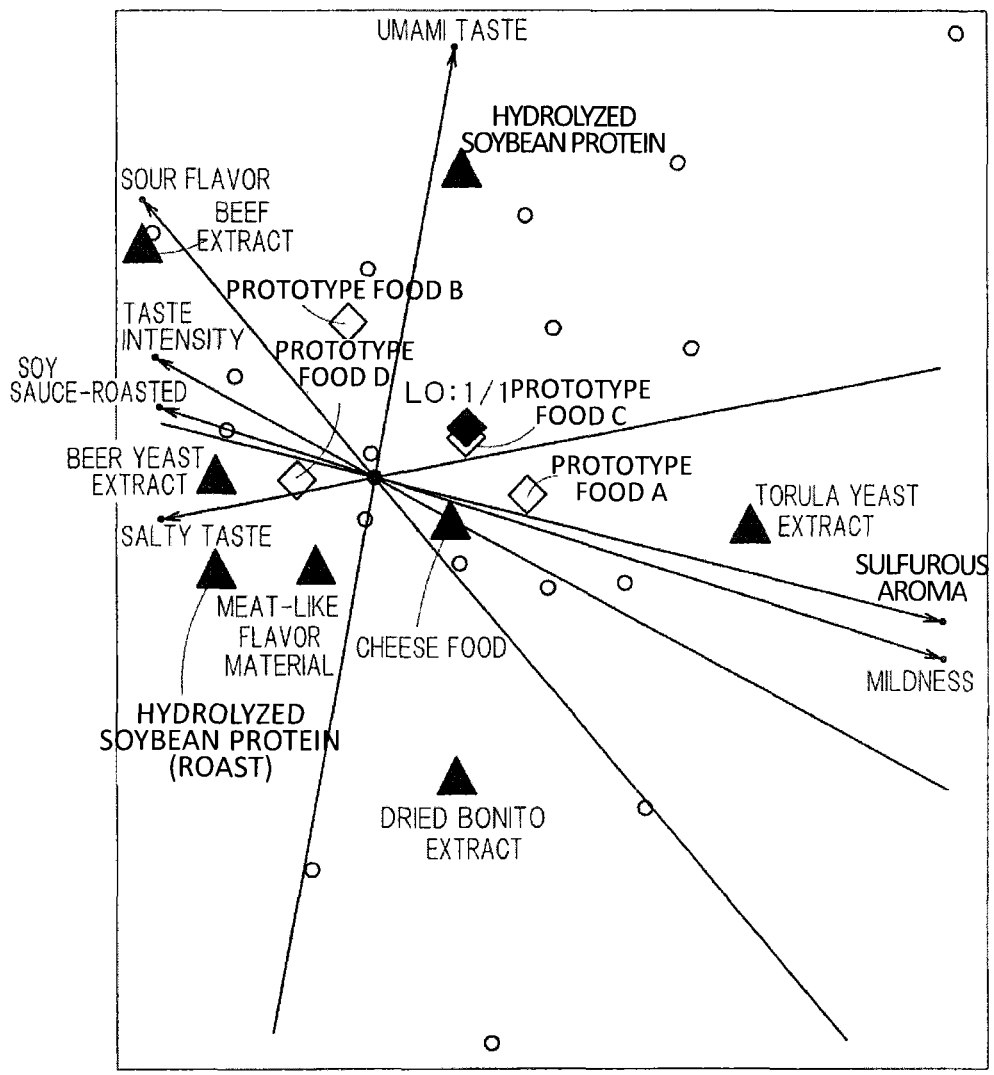
F I G. 17

| TEST MATERIAL | AVERAGE CONSUMPTION RATIO |
|---|---|
| HYDROLYZED SOYBEAN PROTEIN (ROAST) | 71 |
| BEER YEAST EXTRACT | 71 |
| MEAT-LIKE FLAVOR MATERIAL | 76 |
| HYDROLYZED SOYBEAN PROTEIN | 80 |
| TORULA YEAST EXTRACT | 76 |
| BEEF EXTRACT | 76 |
| DRIED BONITO EXTRACT | 69 |
| CHEESE FOOD | 92 |
| PROTOTYPE FOOD A | 86 |
| PROTOTYPE FOOD B | 90 |
| PROTOTYPE FOOD C | 94 |
| PROTOTYPE FOOD D | 88 |

FIG. 18

| FIRST CHOICE | AVERAGE CONSUMPTION RATIO |
|---|---|
| HYDROLYZED SOYBEAN PROTEIN (ROAST) | 67.5 |
| BEER YEAST EXTRACT | 70 |
| MEAT-LIKE FLAVOR MATERIAL | 65 |
| HYDROLYZED SOYBEAN PROTEIN | 82.5 |
| TORULA YEAST EXTRACT | 75 |
| BEEF EXTRACT | 60 |
| DRIED BONITO EXTRACT | 70 |
| CHEESE FOOD | 90 |
| PROTOTYPE FOOD A | 80 |
| PROTOTYPE FOOD B | 95 |
| PROTOTYPE FOOD C | 92.5 |
| PROTOTYPE FOOD D | 90 |

|  | PROTOTYPE FOOD A | HYDROLYZED SOYBEAN PROTEIN | TEST |
|---|---|---|---|
| AVEAGE CONSUMPTION RATIO | 64 | 36 | * |

(b)

|  | PROTOTYPE FOOD C | CHEESE FOOD | TEST |
|---|---|---|---|
| AVEAGE CONSUMPTION RATIO | 60.5 | 39.5 | |

F I G. 20

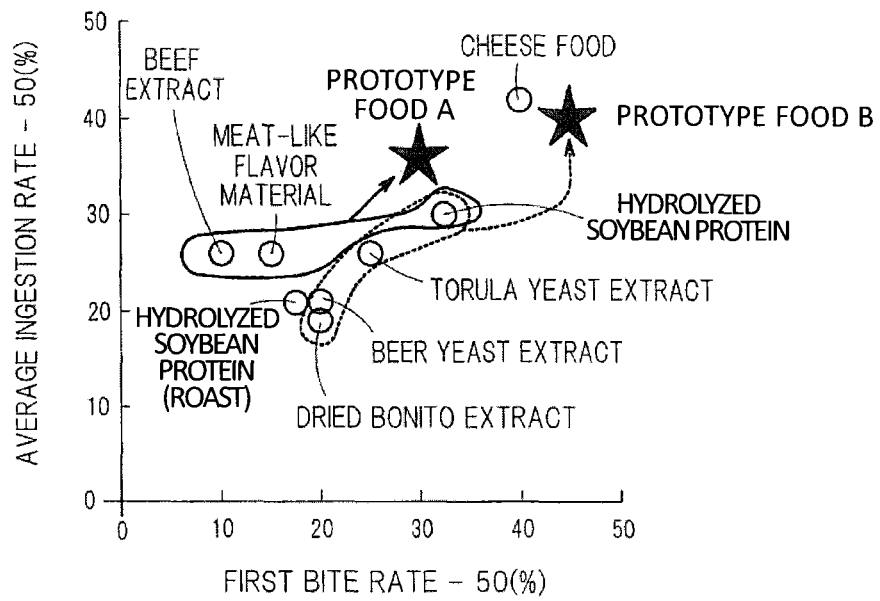
F I G. 21
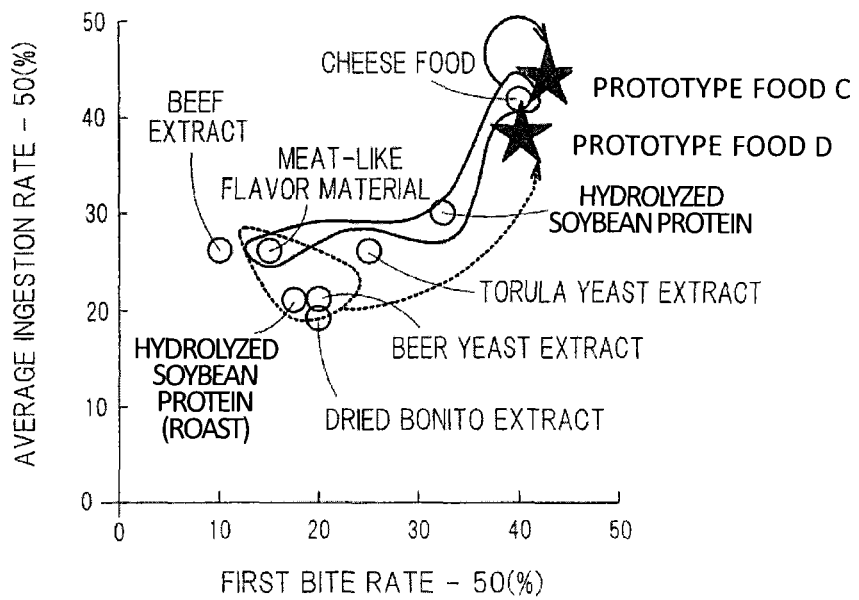
F I G. 22

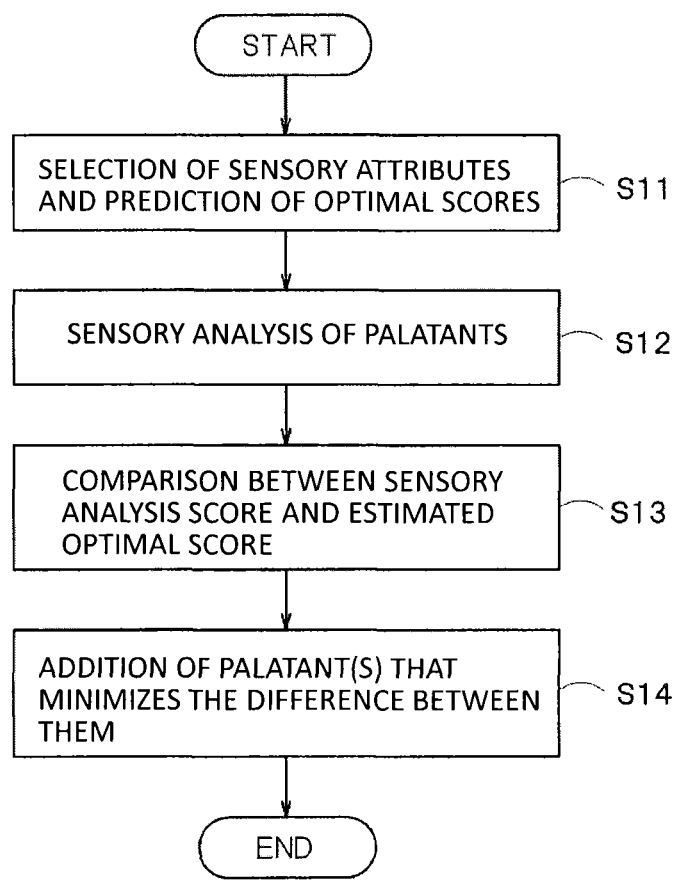
F I G. 23

METHOD FOR EVALUATING FOOD PREFERENCE OF PETS

CROSS-REFERENCE TO RELATED APPLICATIONS

This application is a continuation of and claims the benefits of priority to Japanese Patent Application No. 2013-71564, filed on Mar. 29, 2013, the entire contents of which are incorporated herein by reference.

BACKGROUND

Technical Field

The present invention relates to a method for evaluating food preference of pets, a method for manufacturing an additive for pet foods, a method for evaluating a pet food, a method for improving a pet food, a method for manufacturing a pet food, a program for evaluating food preference of pets, a device for evaluating food preference of pets, a program for evaluating a pet food, and a device for evaluating a pet food, making use of sensory analysis by humans.

Background Art

With the increase in the number of pet owners who consider their pets as a member of their family and an extended pet life due to the advance in animal medical care technique, various pet foods have been manufactured and sold to cope with a variety of needs. Specific examples thereof include pet foods containing the most appropriate nutrients depending on dog breeds, cat breeds, pet age, or the like, and pet foods having a function against specific diseases, such as obesity and allergy. Pet foods must be eaten at an appropriate amount in order to exert their functions effectively. Palatability is therefore a relevant factor and various palatants are incorporated in pet foods.

A two-pan test is a general method for evaluating food preference of pets. According to the two-pan test, two types of pet food are given to pets and which is eaten first or which is eaten in a larger amount is evaluated. However, the obtainable information is only dogs' behaviors about "which is eaten first" or "which is eaten in a larger amount," and thus is quite restricted.

Accordingly, it is currently required to perform a large number of tests that rely on experience and hunch of researchers in order to formulate a pet food meeting the preference of pets, which is not always an efficient operation.

B. Di Donfrancesco et al. ("AN INITIAL LEXICON FOR SENSORY PROPERTIES OF DRY DOG FOOD", *Journal of sensory studies*, 27 (2012) pp. 498-510.) reports the classification of pet foods utilizing the technique for development of human foods. This document describes the technique for categorizing pet foods by performing a sensory analysis of a pet food by humans to score the intensity of appearance, flavor, texture, and/or aroma using sensory expression of humans and then subjecting the data thus obtained to principal component analysis.

B. Di Donfrancesco et al., however, deals only with the categorization of pet foods, and does not address predication or evaluation of food preference of pets, that is, what kind of pet foods is preferred by pets.

Although humans must eat a pet food for a sensory analysis of a pet food itself, eating a pet food is considered to give sometimes a feeling of rejection to humans and to suffer from safety problems.

Furthermore, even if there is no safety problem, it is not always possible to evaluate a pet food precisely because human sensory assessors are not usually involved in a sensory analysis of pet foods. For example, evaluation may vary among sensory assessors.

The present invention is achieved in consideration of the above problems and has an object to provide a method, a program, and a device for evaluating food preference of pets easily and highly precisely even without the need to taste a pet food itself by humans.

Another object of the present invention is to provide a method, a program, and a device for evaluating pet foods; a method for manufacturing an additive for pet foods preferred by pets; a method for improving a pet food so as to be preferred by pets; and a method for manufacturing a pet food preferred by pets by making use of the results of a preference test in pets obtained by the above method.

SUMMARY OF THE INVENTION

One aspect of the present invention provides a method of evaluating a food preference of a pet, including: selecting a plurality of palatants for a pet food; determining a plurality of sensory attributes; performing a sensory analysis of the palatants such that an intensity of each of the sensory attributes is scored for each of the palatants; feeding each of the palatants to a pet such that a preference test is performed on the pet; and analyzing results of the sensory analysis and the preference test such that contributing attributes that contribute to a food preference of the pet are determined from the plurality of sensory attributes.

Another aspect of the present invention provides a method of evaluating a pet food, including: selecting at least a part of palatants included in the pet food; determining a plurality of sensory attributes; performing a sensory analysis of the palatants such that an intensity of each of the sensory attributes is scored for each of the palatants; feeding each of the palatants to a pet such that a preference test is performed on the pet; analyzing results of the sensory analysis and the preference test such that contributing attributes that contribute to a food preference of the pet are determined from the plurality of sensory attributes, the analyzing includes mapping the results of the sensory analysis and the preference test on a spatial coordinate, and calculating an optimal score for each of the contributing attributes; obtaining a sensory analysis score for each of the contributing attributes; and comparing a difference between the sensory analysis score and the optimal score.

Yet Another aspect of the present invention provides a method of producing an additive for pet food, including: selecting a plurality of palatants for a pet food; determining a plurality of sensory attributes; performing a sensory analysis of the palatants such that an intensity of each of the sensory attributes is scored for each of the palatants; feeding each of the palatants to a pet such that a preference test is performed on the pet; analyzing results of the sensory analysis and the preference test such that contributing attributes that contribute to a food preference of the pet are determined from the plurality of sensory attributes, the analyzing includes mapping the results of the sensory analysis and the preference test on a spatial coordinate, and calculating an optimal score for each of the contributing attributes; obtaining a sensory analysis score for each of the contributing attributes; comparing a difference between the sensory analysis score and the optimal score; and mixing a plurality of palatants such that the difference between the sensory analysis score and the optimal score is minimized.

Still another aspect of the present invention provides a method of improving a pet food, including: evaluating a pet food by the above method of evaluating the pet food; and adding a palatant to the pet food such that the difference between the sensory analysis score and the optimal score is minimized.

Further, one aspect of the present invention provides a method of producing a pet food, including: preparing a pet food including at least a base material and palatants; evaluating a pet food by the above method of evaluating the pet food; and adding a palatant to the pet food such that the difference between the sensory analysis score and the optimal score is minimized.

Another aspect of the present invention provides a non-transitory computer-readable medium including computer executable instructions, wherein the instructions, when executed by a computer, cause the computer to perform a method of evaluating a food preference of a pet, including: analyzing results of a sensory analysis of palatants and a preference test of the palatants to identify contributing sensory attributes that contribute to a food preference of a pet, wherein the results of the sensory analysis contain sensory analysis scores showing an intensity of each of the sensory attributes in each of the palatants, the results of the preference test contain preference scores showing palatability of each of the palatants, and the analyzing includes mapping the sensory analysis scores and the preference scores on a spatial coordinate, and identifying the contributing sensory attributes.

Yet another aspect of the present invention provides a device for evaluating food preference of a pet, including: a processor configured to analyze results of a sensory analysis of palatants and a preference test of the palatants to identify contributing sensory attributes that contribute to a food preference of a pet, wherein the results of the sensory analysis contain sensory analysis scores showing an intensity of each of the sensory attributes in each of the palatants, the results of the preference test contain preference scores showing palatability of each of the palatants, and in analyzing the results of the sensory analysis and the preference test, the processor is configured to map the sensory analysis scores and the preference scores on a spatial coordinate, and identify the contributing sensory attributes.

Still another aspect of the present invention provides a non-transitory computer-readable medium including computer executable instructions, wherein the instructions, when executed by a computer, cause the computer to perform a method of evaluating a pet food, including: comparing a difference between a sensory analysis score and an optimal score for each of contributing sensory attributes that contribute to a food preference of a pet, wherein the sensory analysis score shows an intensity of each of the contributing sensory attributes in each of at least one palatant contained in the pet food, and the optimal score shows palatability of each of the at least one palatant.

Yet another aspect of the present invention provides a device for evaluating a pet food, including: a processor configured to compare a difference between a sensory analysis score and an optimal score for each of contributing sensory attributes that contribute to a food preference of a pet, wherein the sensory analysis score shows an intensity of each of the contributing sensory attributes in each of at least one palatant contained in the pet food, and the optimal score shows palatability of each of the at least one palatant.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein:

FIG. 1 is a flow chart showing the procedures of evaluating food preference of pets.

FIG. 2 shows examples of selected palatants.

FIG. 3 shows examples of sensory attributes.

FIG. 4 shows the results of a sensory analysis conducted by a human.

FIG. 5 shows a list of dogs participating in a preference test.

FIG. 6 shows the results of a preference test for each of 18 beagles on each of palatants.

FIG. 7 shows the results of a preference test for each of 19 small breed dogs on each of palatants.

FIG. 8 shows the results of a multivariate analysis conducted on the results of the preference test and the results of the sensory analysis for beagles.

FIG. 9 shows the correlation coefficients of the respective contributing sensory attributes that contribute to the food preference of beagles.

FIG. 10 shows the selected contributing sensory attributes and the estimated optimal scores thereof for beagles.

FIG. 12 shows the selected contributing sensory attributes and the estimated optimal scores thereof for small breed dogs.

FIG. 13 shows the results of a multivariate analysis conducted on the results of the preference test and the results of the sensory analysis for dogs.

FIG. 14 shows the selected contributing sensory attributes and the estimated optimal scores thereof in dogs.

FIG. 15 shows Prototype Foods A to D and the components thereof.

FIG. 16 shows the scores of the contributing attributes for Prototype Foods A to D.

FIG. 17 shows the results of a sensory analysis for Prototype Foods A to D.

FIG. 18 shows the averages of the food consumption ratios for each of the Prototype Foods by beagles.

FIG. 19 shows the results of a "first choice" test of Prototype Foods on beagles.

FIG. 20 shows the results of the comparison tests among Prototype Food A or C and palatants for beagles.

FIG. 21 shows the results of the tests of Prototype Foods A and B and their palatants on beagles.

FIG. 22 shows the results of the tests of Prototype Foods C and D and their palatants on beagles.

FIG. 23 is a flow chart showing the procedures of improving a pet food.

DESCRIPTION OF EMBODIMENTS

Figure 11:
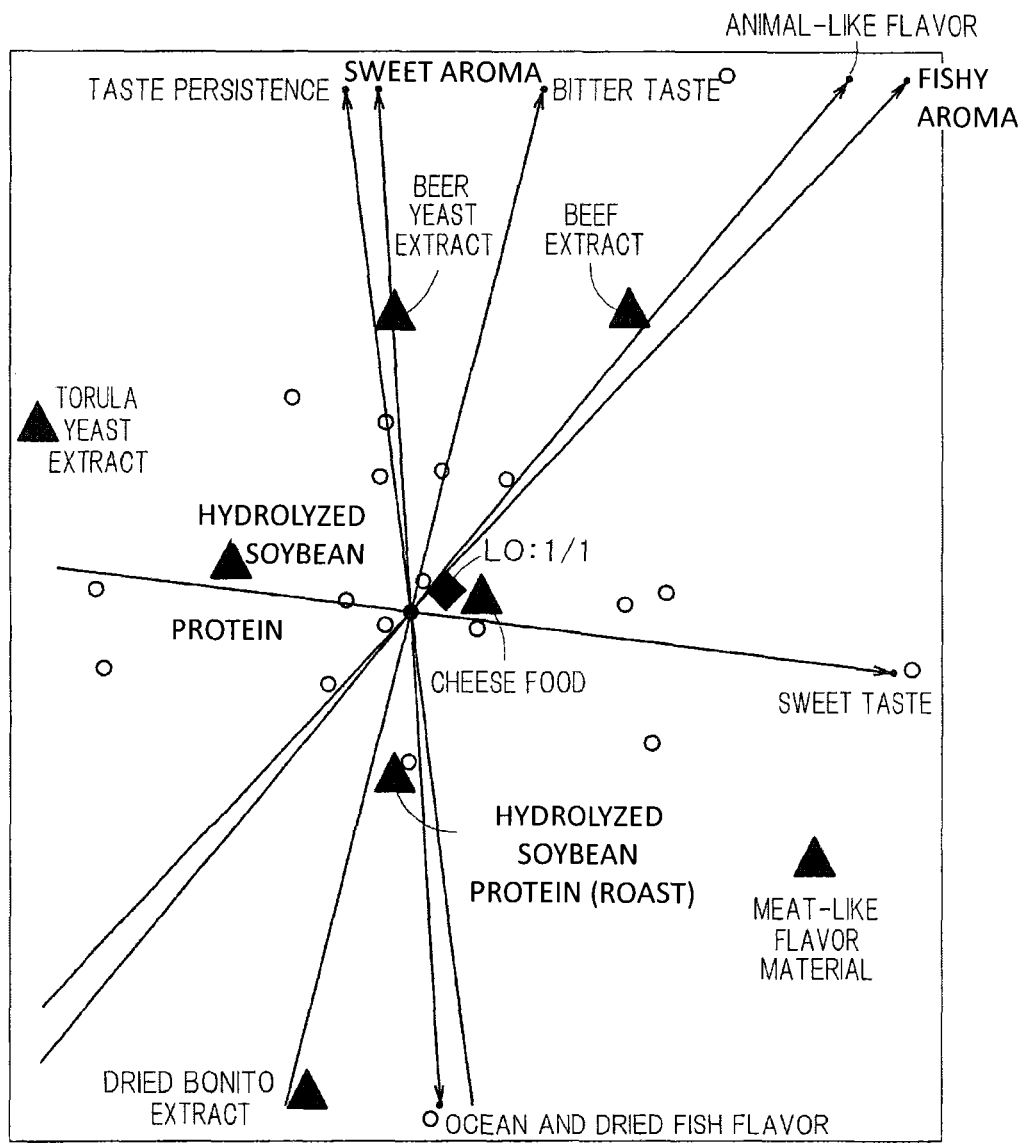
FIG. 11 shows the results of a multivariate analysis conducted on the results of the preference test and the results of the sensory analysis for small breed dogs.

Embodiments of the present invention will be specifically explained referring to the drawings.

First Embodiment

FIG. 1 is a flow chart showing the procedures of evaluating food preference of pets according to one embodiment of the present invention. The preference evaluation can determine at least one sensory attribute that affects food preference of a pet which is a predetermined subject for evaluation (hereinbelow simply referred to as a pet). The preference evaluation can also determine which of the sensory attributes contribute to the food preference and how a pet likes the contributing attributes to be modified one another.

First, at least one palatant contained in a pet food is selected (Step S1). The palatants can be seasonings, seasoning materials, or simply, materials. The palatants can possibly adjust sensory attributes of a pet food or are involved in sensory attributes. Examples of the palatants include livestock products (such as meat, fish, egg, and milk), meat extracts (such as beef, pork, and chicken extracts), protein hydrolysates (those obtained by treating animal protein, such as meat, meat side products (such as internal organs, tendon, bone, and skin) and fish or plant proteins such as soybean, wheat, and corn with an acid or an enzyme to degrade into peptides and amino acids), yeast extracts, fish oils, plant oils, synthetic aromas, sugars, amino acids, Maillard reaction products, table salt, nucleic acids, spices, phosphates, and dairy products (such as yogurt, cream, cheese, and butter). Examples of the sensory attributes include descriptors indicating taste, aroma, and flavor, and can be expressed with terms intuitive to humans. The sensory attributes are a plurality of parameters common to the respective palatants.

It is preferable to select various palatants having various sensory attributes in order to predict or evaluate preference of pets appropriately. In addition, appropriate palatants can be selected depending on the pets. Palatants to be selected may be existing palatants as well as newly prepared palatants. Here, those with no safety problem for human consumption are selected.

Subsequently, a sensory analysis is performed on each of the selected palatants by a human (Step S2). The sensory analysis is conducted to evaluate sensory attributes (evaluation may include, for example, scoring of the intensity of each of the sensory attributes) by an analyst who actually eats palatants for evaluation. The sensory analysis allows evaluation of each of the sensory attributes of the respective palatants.

As one of the features of the present embodiment, the sensory analysis is conducted not necessarily on a pet food itself but on a palatant contained in the pet food. Accordingly, as compared with a sensory analysis by eating a pet food itself, the sensory assessors would feel less reluctant to the sensory analysis and, further, health and safety of the sensory assessors are protected during the sensory analysis. It is preferable that a sensory analysis of a palatant is routinely conducted and sensory assessors are accustomed thereto. Variance among sensory assessors is therefore small, allowing precise evaluation.

In addition, a preference test in pets is conducted on each of the selected palatants (Step S3). The preference test allows scoring of the palatability of the respective palatants for the pets based on "average consumption ratios" or "average food consumption ratios" as described below. Here, Steps S2 and S3 are not necessarily conducted in this order and may also be conducted simultaneously.

Subsequently, preference of pets is predicted or evaluated based on the results of the human sensory analysis and the results of the preference test on pets (Step S4). More specifically, a multivariate analysis is conducted on these two results to determine which of the sensory attributes is a contributing sensory attribute (or sometimes called "contributing attribute") that contributes to or more strongly affects the food preference of pets. Further, an optimal score that corresponds to the preference of pets is calculated for each of the contributing attributes. The processing in Step S4 can be conducted by instructing a prediction device such as a computer and a taste sensing system to execute a program for predicting the preference of pets.

As a result of the evaluation, a contributor to the preference of pets can be identified as a contributing sensory attribute. Therefore, the sensory attributes contributing to the preference of pets (i.e., contributing attributes) can be expressed in terms of sensory expressions by humans and their optimal scores can be estimated.

Subsequently, a prototype food is prepared based on the results of Step S4 in order to confirm that the preference of pets is appropriately evaluated (Step S5). In other words, the optimal score for the contributing attribute calculated in Step S4 may be set to be a target value, and more than one palatants are blended to prepare a prototype food having the closest possible value to the target value. A prototype food may be prepared by, for example, adjusting the palatants to be blended and/or the blending ratios thereof through repeated sensory analyses by humans. The results of the preference test in Step S2 can be utilized in this preparation operation. A prototype food may be prepared using only the palatants selected in Step S1 or using other palatants.

A test to determine whether a prototype food is preferred by pets is then conducted (Step S6). In this test, a test similar to the preference test in Step S3 is preferably conducted. This allows confirmation that the pets prefer the prototype food to a palatant given alone.

When a prototype food is confirmed as preferred by pets, the prototype food may be used as a pet food or an additive for pet foods, which may be sprinkled on an existing pet food. Sprinkling the additive on an existing pet food can make the existing pet food more preferred by pets. Palatants and the additives may be blended using a blending apparatus for mass production, based on the materials to be blended and their blending ratios determined in the previous steps.

An example of prediction conducted on dogs will be specifically explained below.

First, as Step S1 in FIG. 1, eight palatants shown in FIG. 2: (1) roast flavor type hydrolyzed soybean protein (hereinbelow simply referred to as "hydrolyzed soybean protein (roast)"), (2) beer yeast extract, (3) meat-like flavor material, (4) hydrolyzed soybean protein, (5) torula yeast extract, (6) beef extract, (7) dried bonito extract, and (8) cheese paste were selected. The palatants which differed from each other in terms of taste, aroma, and flavor were selected in order to evaluate various sensory attributes as much as possible.

Subsequently, as Step S2 in FIG. 1, sensory analysis by a human is performed. In the exemplary sensory analysis, sensory assessors tasted solutions containing each of six palatants other than beef extract and dried bonito extract shown in FIG. 2 at 2% (w/w). Since the undiluted solutions of two palatants, beef extract and dried bonito extract, were 50% (w/w) solutions, the sensory assessors tasted solutions containing each palatant at 4% (w/w).

The sensory assessors listed all terms they thought of for taste, aroma and flavor. Terms highly similar to each other were then grouped together into some meaningful categories according to the KJ method (also called or well known as affinity diagram or affinity chart), and 18 descriptors were extracted as sensory attributes, which are shown in FIG. 3. The sensory attributes included eight sensory attributes indicating taste: sour taste, bitter taste, salty taste, sweet taste, umami taste, mildness, taste intensity, and taste persistence; six sensory attributes indicating aroma: sour aroma, fermentation aroma, roast aroma, sweet aroma, fishy aroma, and sulfurous aroma; and four sensory attributes indicating flavor: soy sauce-roasted flavor, ocean and dried fish flavor, animal-like flavor, and sour flavor.

Sensory analysis was performed according to a five-point scaling method with the criteria consisting of point 1 (very weak) to point 5 (very strong) by sensory assessors for each of these sensory attributes for each of the palatants. Based on the discussion by 3 to 5 sensory assessors, an evaluation score was determined by the consensus QDA (Consensus Descriptive Analysis) for each of the sensory attributes for each of the palatant. The results are shown in FIG. 4.

A preference test on dogs was further conducted as Step S3 in FIG. 1. The dogs consisted of 18 beagles and 19 small breed dogs, and the details concerning the age and sex of these dogs are shown in FIG. 5. "A small breed dog" used herein refers to a dog breed whose average body weight is less than 10.0 kg. Examples of small breed dogs include, but are not limited to, a shih-tzu, a chihuahua, a toy poodle, a pomeranian, a miniature dachshund and a yorkshire terrier. Laboratory Animal feed DS-A manufactured by Oriental Yeast Co., Ltd. (hereinbelow referred to as DS-A) was used as a base material in prototype foods for the preference test. DS-A is a blank food with little taste, aroma, or flavor.

A two-pan test was used for the preference test. More specifically, the dogs each housed in an individual breeding cage were given a food containing no palatant ("a control food") and a food containing a palatant ("a test food") simultaneously at predetermined amounts. The food containing no palatant is DS-A to which no palatant is added, and the food containing a palatant is DS-A to which a palatant is added at 0.2% (w/w) by spraying in the form of fine mist. The above predetermined amounts are 250 g for beagles and 100 g for small breed dogs.

The two-pan test was finished when one of the control food and the test food was completely eaten or when a predetermined period of time had passed. The predetermined periods of time are 20 minutes for beagles and 60 minutes for small breed dogs.

An average food consumption ratio at the completion of the test was then calculated. The average consumption ratio is defined by the following formula (I).

(Average food consumption ratio)=(Amount of the test food eaten)/((amount of the test food eaten)+(amount of the control food eaten))× 100%  (1)

The preference for each dog for each palatant was scored in 11 grades by rounding up the average consumption ratio to the nearest 10 and the obtained score was used as a preference score. For example, the consumption ratio of 0% is expressed as "1," that of 50% as "6," that of 78% as "9," which was obtained by rounding a unit digital of 78% to raise to 80%, and that of 100% as "11." The testing period was two days, and the positions where the control food and the test food were placed were alternated each day to avoid position eater tendencies.

The 11-grade preference scores for palatability of each of the palatants by each of the 18 beagles are shown in FIG. 6. The 11-grade preference score for palatability of each of the palatants by each of the 19 small breed dogs are shown in FIG. 7.

Subsequently, food preference of dogs was evaluated as Step S4 in FIG. 1. In this case, Landscape Segmentation Analyses (LSA®, registered trademark), one of the preference mapping techniques applying a multivariate analysis method, was conducted to overlay the results of the preference test in dogs on the diagram of the sensory analysis results by humans. In this analysis, IFPrograms™ (registered trademark), a software manufactured by Institute for Perception in the U.S., was used.

FIG. 8 is an exemplary figure for explaining the technique for evaluating the preference of beagles. The evaluation method will be specifically explained below referring to the figure.

First, distances of each of the individuals (18 beagles) and each of the palatants (8 materials) from the Ideal Point were calculated based on the data in FIG. 6. The Ideal Point, if present, is a coordinate value that represents an ideal palatant which is determined as most preferred by the individual subjects and has a full mark (evaluation score of 11). The relative relation between an individual and a palatant obtained was plotted to a three-dimensional space while paying attention not to lose information as far as possible. A Subject R square value and a Product R square value were used as the indices to know the amount of information which was lost during the plotting process. These values indicates correlation coefficients between the original data and the coordinate values for an individual (Subject) and a material (Product) in the three-dimensional space, respectively. As a result, the Subject R square value is 0.777 and the Product R square value is 0.940, and the map can thus be said to be plotted appropriately. Eighteen open circles indicate the individual dogs and eight solid triangles indicate the palatants in FIG. 8.

The three-dimensional space thus obtained shows the relation between each individual and each palatant by a distance. For example, it is shown that when the distance between an open circle and a solid triangle is closer, the individual dog indicated by the open circle more strongly prefers the palatant indicated by the solid triangle.

Then, the correlation (arrows in FIG. 8) between the results of the sensory analysis by humans, that is, the sensory analysis scores for the 18 sensory attributes (FIG. 4), and the palatants was calculated based on the three-dimensional space thus obtained. The correlation coefficients between the sensory analysis scores of the respective sensory attributes and the spatial coordinate of the palatants are shown in FIG. 9. Eight sensory attributes with a statistical significance ($p<0.05$) were sour taste, salty taste, umami taste, mildness, taste intensity, sulfurous aroma, soy sauce-roasted flavor and sour flavor, which were then determined as the sensory attributes contributing to or strongly affecting the food preference of beagles. These contributing sensory attributes can be viewed as the factors relevant to the preference of pets, and can be suitably used to explain the preference of beagles in human words.

Further, one point (a solid square in FIG. 8) where the distance is the smallest from all the individuals in the three-dimensional space was identified as an LO (Linking Optimum). The optimal score for each of the contributing attributes was calculated by regressing the coordinate of the LO to the contributing attribute. The optimal score thus calculated is the estimated optimal score for each of the contributing attributes that reflects the preference of beagles.

The results of the preference evaluation of beagles are shown in FIG. 10. It was estimated that the eight contributing attributes in the left column in FIG. 10 are the sensory attributes more strongly affecting the preference of beagles, and that the contributing attributes having the scores shown in the right column are optimal and most preferred for beagles.

According to the results, beagles are shown to prefer, in terms of taste, relatively weak sour and salty taste and intermediate levels of umami taste, mildness, and taste intensity. It is also shown concerning taste that other sensory attributes such as bitter taste and sweet taste do not largely affect the preference of beagles. Similar findings were obtained in terms of aroma and flavor. As described above, the preference of beagles can be expressed in human sensory words according to the present embodiment.

A similar palatability evaluation was conducted in small breed dogs. The results are shown in FIGS. 11 and 12. As shown in the figures, seven sensory attributes were contributing to or strongly affecting the food preference of small breed dogs. There were no contributing attributes that were common between the beagles and the small breed dogs.

Although the evaluations were made separately in the 18 beagles and the 19 small breed dogs, the results may also be obtained from those of the preference test in 37 dogs so as to determine the preference of "dogs" without separating beagles or small breed dogs from the others. The results of the palatability evaluation on the dogs are shown in FIGS. 13 and 14. In FIG. 13, an open circle represents a small breed dog and a shaded circle represents a beagle. The eight contributing attributes shown in the figures were more relevant to the dogs. Among these, four factors were common to the beagles and three factors were common to the small breed dogs.

The preference of beagles and small breed dogs was found as described above. Then, as Step S5 in FIG. 1, prototype foods having the compositions meeting the preference of beagles were prepared as follows. First, the selected palatants were classified into a taste material and a flavor material. A 2% (w/w) solution of a taste material was then mixed with a 2% (w/w) solution of a flavor material at a ratio of 1:1, and a human tasted the mixture to evaluate each of the contributing attributes for beagles. Another palatant was then added to make the scores for the respective contributing attributes closer to the predicted optimal scores for beagles shown in FIG. 10 and determine a blending ratio of the palatants suitable for beagles. Prototype foods A to D having the compositions closer to the preference of beagles were prepared by such an operation. The components and blending ratios thereof in Prototype Foods A to D are shown in FIG. 15.

The scores of the contributing attributes for Prototype Foods A to D are shown in FIG. 16. The score for Prototype Foods A to D are overlaid onto the diagram shown in FIG. 8 to obtain the diagram shown in FIG. 17. As shown in these figures, all the prototype foods are shown to have scores close to the estimated optimal scores for beagles.

Subsequently, as Step S6 in FIG. 1, a test was conducted in 20 beagles based on the 2-pan test shown in Step S3, where Prototype Foods A to D were evaluated as test foods. The results of the test are shown in FIG. 18. FIG. 18 shows the average consumption ratio in the 20 beagles for the respective palatants and Prototype Foods A to D.

The average consumption ratio was as high as 86% or above for all of Prototype Foods A to D. Prototype Food A contained dried bonito extract, hydrolyzed soybean protein, and torula yeast extract as palatants. The average consumption ratio for Prototype Food A was higher than those of all these palatants. The same can be applied to Prototype Foods B to D.

A first choice test was also conducted in addition to the above mentioned test. The proportion of the beagles that first ate the food containing palatant(s) with respect to all 20 beagles was calculated in the test. The food containing no palatant was used as a control. The results of the first choice test are shown in FIG. 19. The ratio of the beagles that first ate the food containing palatants was as high as 80% or above for all Prototype Foods A to D. Although the proportion for Prototype Food A was slightly lower than that for the hydrolyzed soybean protein, the ratio for Prototype Food A was higher than those for the dried bonito extract and the torula yeast extract. The ratio was higher for Prototype Foods B to D than those for all the constituent palatants. Then, Prototype Foods A to D are found to be preferred by beagles.

Further, in order to confirm the above results, comparative tests based on the 2-pan test in beagles were conducted between Prototype Food A and the hydrolyzed soybean protein given alone and between Prototype Food C and cheese food given alone. The results of the tests are shown in FIG. 20. A paired t-test was used to evaluate whether there was a significant difference. The results show that at least Prototype Food A was significantly more preferred than the hydrolyzed soybean protein given alone ($p<0.05$). Prototype Food C was also suggested to be more preferred than the cheese food given alone.

FIG. 21 compares the test results among Prototype Food A, Prototype Food B, and each of the constituent palatants thereof. FIG. 22 compares the test results among Prototype Food C, Prototype Food D, and each of the constituent palatants thereof. The abscissa axis in both figures indicates the scores obtained by subtracting 50% from the ratio of the first choice and the ordinate indicates the scores obtained by subtracting 50% from the average consumption ratio. Points plotted closer to the upper right corner correspond to more preference by beagles.

FIGS. 21 and 22 also show that Prototype Foods A to D are more preferred by beagles than their constituent palatants given alone.

Based on the above results, it was suggested that the results of the palatability evaluation in Step S4 were appropriate. It was also found that Prototype Foods A to D are useful as additives for pet foods.

As described above, in the first embodiment, preference of pets is evaluated by conducting a sensory analysis of the constituent palatants by humans. Accordingly, the preference of pets can be highly precisely evaluated by a more simple and intuitive method using sensory attributes for humans. In addition, humans are not necessarily required to eat a pet food itself, because the sensory analysis can be performed on each of the constituent palatants.

The above explanation is merely an example. For example, pets to be evaluated may be other dogs such as large breed dogs or other animals such as cats. In such a case, palatants that affect the preference of the pets may be selected in Step S1 in FIG. 1. For example, when the preference of cats is to be evaluated, the palatants shown in FIG. 2 are not necessarily selected and palatants considered to be preferred by cats may be selected. With regards to sensory attributes, only some of the sensory attributes shown in FIG. 3 may be used and other sensory attributes may be used.

Second Embodiment

The sensory attributes contributing to the preference of pets and their estimated optimal scores could be expressed by sensory expression by humans in the first embodiment. In the second embodiment, a pet food is improved based on the contributing sensory attributes and their predicted optimal scores thus obtained. In the second embodiment, the invention relates to a method for making pet food base materials more preferred by pets. In this embodiment, palatants are added to a pet food to adjust sensory attributes of the food.

The outline of the general pet food manufacturing method is described below. First, raw materials that have been roughly crushed into a certain particle size in advance are supplied to an extruder and subjected to extrusion molding to prepare a base material (kibbles). The base material is coated with oil/fat and then additives are added. Examples of the additives include antioxidants and palatants. The method for improving such a pet food according to one embodiment of the invention will be explained below.

FIG. 23 is a flow chart showing the procedures of improving a pet food. First, sensory attributes that contribute to the target pets (contributing sensory attributes) are determined and the optimal scores are estimated for the respective contributing sensory attributes (Step S11) in accordance with the method described in the first embodiment. The calculation of the optimal scores may be only once, and the calculation at each occasion of improvement of a pet food is not necessarily required. Further, Step S11 in FIG. 23 and the subsequent steps may be conducted by other persons. For example, the estimated optimal scores obtained by one person may be used by another person.

A sensory analysis by humans is conducted on palatants contained in a pet food to be improved (Step S12). The specific method of the sensory analysis may be similar to that in Step S2 in FIG. 1. Here, only the palatants included in the additives or the pet food may be evaluated, or when palatants are contained in raw materials or a fat/oil coating, evaluation may also be performed on these palatants or a fat/oil coating. When the palatants that strongly affect the preference of pets are known, only such palatants may be evaluated. However, since humans perform the sensory analysis, the evaluation is made only on the palatants that have no safety problem for human consumption.

For the palatants and the base materials which have a safety or health problem, a taste sensor (TS-5000Z, manufactured by Intelligent Sensor Technology Inc.) may be used for evaluation, and the results thus obtained by a taste sensor may be taken into consideration to adjust the results of the sensory analysis on palatants by human.

Subsequently, a difference between the sensory analysis score for each contributing attribute in a palatant obtained by the sensory analysis and the estimated optimal score for the contributing attribute (in Step S11) is evaluated by comparison (Step S13). This comparison is performed by overlaying the results of the evaluation of the palatants on, for example, the diagram as shown in FIG. 8. A smaller difference between the result of the evaluation of a palatant and the LO means that the palatant is more preferred by pets. Therefore, a method according to one embodiment of the present invention may further comprise a step of evaluating the difference between the sensory analysis score and the estimated optimal score for each contributing sensory attribute.

The comparison of the sensory analysis score and the estimated optimal score therefore allows one to consider improvement in pet foods using sensory expression by humans, such as "it is better to make sour taste stronger," or "it is better to make sulfurous aroma weaker." Alternatively, one may think of the improvement by selecting a specific palatant, such as "it is better to add hydrolyzed soybean protein (roast) in order to enhance sour taste," based on FIG. 4. The palatants to be selected may be those not included in a pet food or those which are included in a pet food and may be used in a greater amount.

The evaluation in Step S13 may be conducted by a human or with a pet food evaluation device, such as a computer, by instructing the device to execute a pet food evaluation program.

One may provide a proposal for improving a pet food, for example, to a third party company. Further, a pet food may be improved by adding one or more palatants so as to further minimize a difference between the sensory analysis score and the estimated optimal score of the contributing attributes in the palatants, in other words, so as to make the sensory analysis score closer to a target value, which is the calculated optimal score (Step S14). The palatants may be added by a human or a device. An improved pet food can be thereby manufactured.

Figure 24:
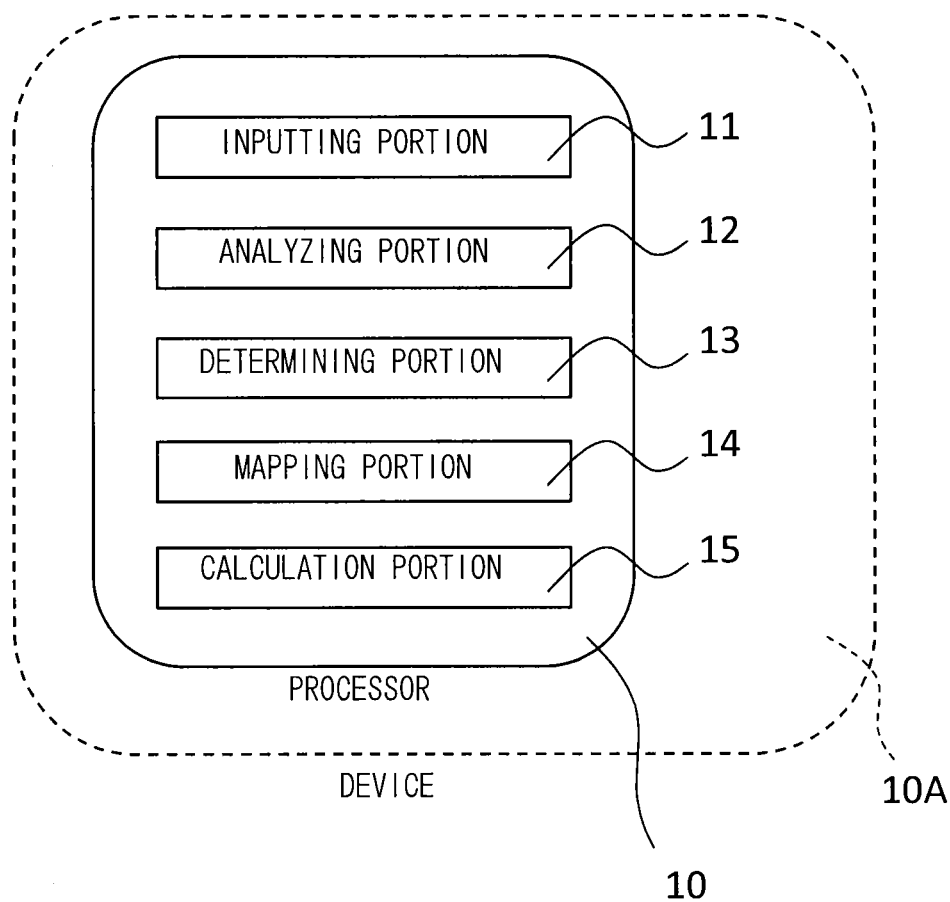
FIG. 24 is a diagram illustrating an exemplary configuration of an evaluation device according to one embodiment of the present invention.
Figure 25:
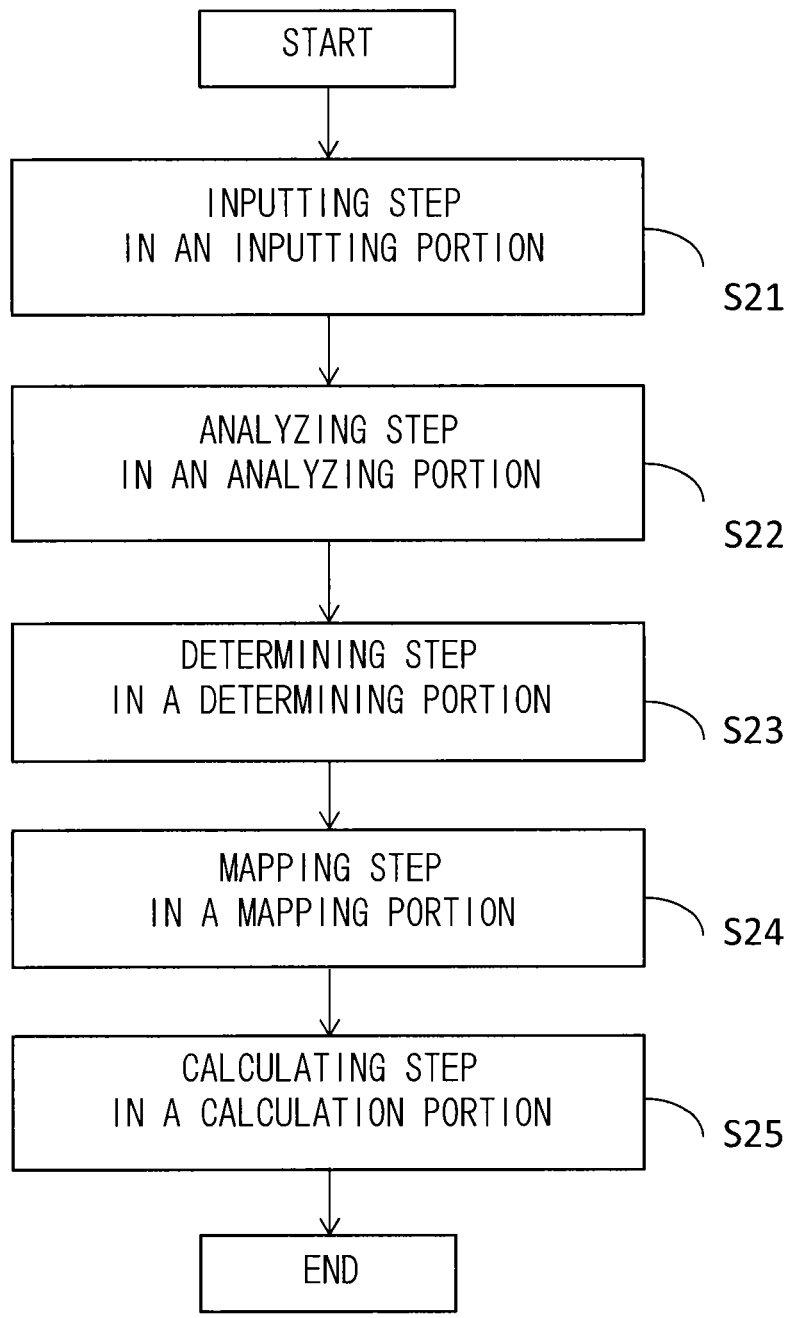
FIG. 25 is a flow chart showing an exemplary process implemented by an evaluation device according to one embodiment of the present invention.

A device (10A) for evaluating food preference of a pet is also provided according to one embodiment of the invention. Referring to FIGS. 24 and 25, a device (10A) comprises a processor (10) configured to analyze results of a sensory analysis of palatants and a preference test of the palatants (analyzing step: S22) in an analyzing portion (12), and determine contributing sensory attributes that contribute to a food preference of a pet (determining step: S23) in a determining portion (13). The processor in another embodiment may further be configured to map the sensory analysis scores (mapping step: S24) in a mapping portion (14) and calculate an optimal score for each of the contributing sensory attributes (calculating step: S25) in a calculating portion (15) to evaluate a pet food. The results of a sensory analysis of palatants contain sensory analysis scores showing an intensity of each of the sensory attributes in each of the palatants. The results of a preference test of the palatants contain preference scores showing palatability of each of the palatants. These results may be input into the processor (10) (inputting step: S21) via an inputting portion (11).

As described above, a pet food can be improved by adding one or more palatants, based on the contributing attributes in the palatants and their estimated optimal scores in the second embodiment. In addition, since the predicted optimal score is expressed by a numerical value, a pet food can be improved based on the numerical value. In addition, the method according to one embodiment of the present invention allows one to propose an appropriate improvement method and palatants to efficiently improve a pet food without the need of random screening of palatants.

At least some parts of the determination, prediction or evaluation of the preference of pets described in the above embodiment may be performed by a hardware or by a software. For a software, a program that implements at least some of the functions of the determination, prediction or evaluation may be stored in a recording medium such as a flexible disc or CD-ROM and read by a computer to allow execution. The recording medium is not limited to a removable medium such as a magnetic disc or an optical disc and may be a fixed recording medium such as a hard disk device or a memory.

A program that implements at least some parts of the functions of the determination, prediction or evaluation of the preference of pets may also be distributed through a communication line (including radio communication) such as internet. Further, the program may be distributed in a coded, modulated, or compressed state through a wired line or a wireless line such as internet or by storing in a recording medium.

As described above, one aspect of the present invention provides a method for predicting liking of pets comprising the steps of: performing a preference test in pets on more than one palatant for a pet food, wherein the palatants have been selected in advance (testing step); and selecting as a driver for pet liking a sensory attribute that strongly affects liking of pets based on the results of the preference test in pets and the results of a sensory analysis by humans conducted in advance, the results of the sensory analysis being obtained by scoring the intensity of each of sensory attributes for the palatants by humans (evaluation step).

Further, one aspect of the present invention provides a method for evaluating a pet food comprising the steps of: scoring the intensity of a predetermined driver for pet liking for at least part of palatants contained in the pet food; and calculating and evaluating a difference between the intensity and a predicted optimal score for the driver for pet liking, wherein the driver for pet liking and the optimal score are obtained based on the results of a preference test in pets performed on more than one palatant and the results of a sensory analysis by humans, the results of the sensory analysis being obtained by scoring the intensity of each of sensory attributes for the palatants by humans.

Further, one aspect of the present invention provides a method for manufacturing an additive for pet foods comprising: manufacturing an additive for pet foods by mixing more than one palatant for pet foods so as to minimize a difference between the scored intensity and the predicted optimal score for a predetermined driver for pet liking, wherein the driver for pet liking and the optimal score are obtained based on the results of a preference test in pets performed on more than one palatant and the results of a sensory analysis by humans, the results of the sensory analysis being obtained by scoring the intensity of each of sensory attributes for the palatants by humans.

Further, one aspect of the present invention provides a method for improving a pet food by further adding a palatant to a pre-improvement pet food comprising at least a base material and palatants comprising: a step of scoring the intensity of a predetermined driver for pet liking for at least part of the palatants contained in the pre-improvement pet food; and a step of adding to the pre-improvement pet food a palatant that minimizes a difference between the intensity and a predicted optimal score for the predetermined driver for pet liking, wherein the driver for pet liking and the optimal score are obtained based on the results of the preference tests in pets performed on more than one palatant and the results of a sensory analysis by humans, the results of the sensory analysis being obtained by scoring the intensity of each of sensory attributes for the palatants by humans.

Further, one aspect of the present invention provides a method for manufacturing an improved pet food by further adding a palatant to a pre-improvement pet food comprising at least a base material and palatants comprising: a step of scoring the intensity of a predetermined driver for pet liking for at least part of the palatants contained in the pre-improvement pet food; and a step of adding to the pre-improvement pet food a palatant that minimizes a difference between the intensity and the predicted optimal score for the predetermined driver for pet liking, wherein the driver for pet liking and the optimal score are obtained based on the results of a preference test in pets performed on more than one palatant and the results of a sensory analysis by humans, the results of the sensory analysis being obtained by quantitatively evaluating each of sensory attributes for the palatants by humans.

Further, one aspect of the present invention provides a program for predicting liking of pets, which makes a computer execute a prediction step of selecting as a driver for pet liking a sensory attribute that strongly affects liking of the pets based on the results of a preference test in the pets and the results of a sensory analysis by humans performed on more than one palatant for a pet food, wherein the palatants have been selected in advance, the results of the sensory analysis being obtained by scoring the intensity of each of sensory attributes for the palatants by humans.

Further, one aspect of the present invention provides a device for predicting liking of pets comprising: a prediction means for selecting as a driver for pet liking a sensory attribute that strongly affects liking of the pets based on the results of a preference test in the pets and the results of a sensory analysis by humans performed on more than one palatant for a pet food, wherein the palatants have been selected in advance, the results of the sensory analysis being obtained by scoring the intensity of each of sensory attributes for the palatants by humans.

Further, one aspect of the present invention provides a program for evaluating a pet food, which makes a computer execute a step of calculating a difference between the scored intensity and the predicted optimal score for a predetermined driver for pet liking, wherein the scored intensity is obtained by scoring the intensity of the predetermined driver for pet liking for at least part of palatants contained in the pet food, and wherein the driver for pet liking and the optimal score are obtained, based on the results of a preference test in pets and the results of a sensory analysis by humans performed on more than one palatant, the results of the sensory analysis being obtained by scoring the intensity of each of sensory attributes for the palatants by humans.

Further, one aspect of the present invention provides a device for evaluating a pet food comprising: an evaluation means for evaluating a difference between the scored intensity and the predicted optimal score for a predetermined driver for pet liking, wherein the scored intensity is obtained by scoring the intensity of each of sensory attributes for at least part of palatants contained in the pet food, based on the results of a preference test in pets and the results of a sensory analysis by humans performed on more than one palatant, the results of the sensory analysis being obtained by scoring the intensity of each of sensory attributes for the palatants by humans.

According to one aspect of the present invention, food preference of pets can be easily and highly precisely predicted or evaluated because an sensory analysis by humans is conducted on each of palatants for pet foods, to which materials humans are accustomed, not on a pet food itself.

The procedures and routines described herein can be embodied as a system, method or computer program product, and can be executed via one or more dedicated circuits or programmed processors. Accordingly, the descriptions provided herein may take the form of exclusively hardware, exclusively software executed on hardware (including firmware, resident software, micro-code, etc.), or through a combination of dedicated hardware components and general processors that are configured by specific algorithms and process codes. Hardware components are referred to as a "circuit," "module," "unit," "device," or "system." Executable code that is executed by hardware is embodied on a tangible memory device, such as a computer program product. Examples include CDs, DVDs, flash drives, hard disk units, ROMs, RAMs and other memory devices.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

As used herein the words "a" and "an" and the like carry the meaning of "one or more." A person skilled in the art may conceive additional effects and various modifications of the present invention based on the above description, and the aspects of the present invention are not limited by the individual embodiments described above. Various additions, modifications, and partial deletions are possible within the range that do not deviate from the conceptional idea and intention of the present invention introduced from the contents defined in the claims and its equivalent.

What is claimed is:

1. A method of evaluating a food preference of a dog, the food preference being expressed in human sensory words, the method comprising:
    selecting a plurality of palatants, where the plurality of palatants includes a roast flavor type hydrolyzed soybean protein, a beer yeast extract, a meat-like flavor material, a hydrolyzed soybean protein, a torula yeast extract, a beef extract, a dried bonito extract, and a cheese paste;
    determining a plurality of sensory attributes indicating taste, aroma, and flavor, where the sensory attributes indicating taste consist of sour taste, bitter taste, salty taste, sweet taste, umami taste, mildness, taste intensity, and taste persistence, the sensory attributes indicating aroma consist of sour aroma, fermentation aroma, roast aroma, sweet aroma, fishy aroma, and sulfurous aroma, and the sensory attributes indicating flavor consist of soy sauce-roasted flavor, ocean and dried fish flavor, animal-like flavor, and sour flavor;
    performing a sensory analysis of the palatants on a human such that the human tastes each of the palatants and scores an intensity of each of the sensory attributes as a sensory analysis score for each of the palatants;
    feeding each of the palatants to a plurality of dogs such that a preference test is performed on the dogs;
    generating a three-dimensional map including plots indicating the dogs and plots indicating the palatants based on results of the preference test, such that each dogs' preference on each of the palatants is indicated by a distance between coordinates of the plots indicating the palatants and coordinates of the plots indicating the dogs, respectively;
    selecting contributory attributes from the sensory attributes showing a statistically significant correlation with at least one of the palatants;
    drawing arrows indicating a respective one of the contributory attributes in the three-dimensional map, based on the sensory analysis score;
    determining a coordinate of a linking optimum (LO) in the three-dimensional map such that a total of distances between the coordinate of the LO and each of the coordinates of the plots indicating the dogs is minimized; and
    calculating an optimal score for each of the contributory attributes by regressing the coordinate of the LO to coordinates of plots indicating each of the palatants,
    wherein the human tastes only the palatants in the method.

2. The method of claim 1, wherein the plurality of dogs is a plurality of small breed dogs.

3. The method of claim 1, wherein the feeding comprises feeding each of the plurality of dogs a pet food not comprising a palatant and pet foods comprising each of the palatants, and the optimal score is calculated by a multivariate analysis.

4. A method of improving a pet food, comprising:
    evaluating a food preference of a dog by the method of claim 1; and
    adding a palatant to the pet food such that the difference between the sensory analysis score for each of the palatants and the optimal score for each of the contributory attributes is minimized,
    wherein the pet food before adding the palatant comprises at least one palatant selected from the group consisting of a roast flavor type hydrolyzed soybean protein, a beer yeast extract, a meat-like flavor material, a hydrolyzed soybean protein, a torula yeast extract, a beef extract, a dried bonito extract, and a cheese paste.

5. A method of producing a pet food, comprising:
    preparing a base food comprising a base material and at least one palatant selected from the group consisting of a roast flavor type hydrolyzed soybean protein, a beer yeast extract, a meat-like flavor material, a hydrolyzed soybean protein, a torula yeast extract, a beef extract, a dried bonito extract, and a cheese paste;
    evaluating a food preference of a dog by the method of claim 1; and
    adding a palatant to the base food such that the difference between the sensory analysis score for each of the palatants and the optimal score for each of the contributory attributes is minimized.

6. The method of claim 1, wherein the plurality of dogs is a plurality of beagle dogs.

7. The method of claim 1, wherein the method consists of the selecting of the plurality of palatants, the determining of the plurality of sensory attributes, the performing of the sensory analysis of the palatants, the feeding of each of the paltants, the generating of the three-dimensional map, the selecting of the contributory attributes, the drawing of the arrows, the determining of the LO, and the calculating of the optimal score.

8. A method of visualizing a food preference of a dog, comprising:
    selecting a plurality of palatants, where the plurality of palatants includes a roast flavor type hydrolyzed soybean protein, a beer yeast extract, a meat-like flavor material, a hydrolyzed soybean protein, a torula yeast extract, a beef extract, a dried bonito extract, and a cheese paste;
    determining a plurality of sensory attributes indicating taste, aroma, and flavor, where the sensory attributes indicating taste consist of sour taste, bitter taste, salty taste, sweet taste, umami taste, mildness, taste intensity, and taste persistence, the sensory attributes indicating aroma consist of sour aroma, fermentation aroma, roast aroma, sweet aroma, fishy aroma, and sulfurous aroma, and the sensory attributes indicating flavor consist of soy sauce-roasted flavor, ocean and dried fish flavor, animal-like flavor, and sour flavor;

performing a sensory analysis of the palatants on a human such that the human tastes each of the palatants and scores an intensity of each of the sensory attributes as a sensory analysis score for each of the palatants;

feeding each of the palatants to a plurality of dogs such that a preference test is performed on the dogs;

generating a three-dimensional map including plots indicating the dogs and plots indicating the palatants based on results of the preference test, such that each dogs' preference on each of the palatants is indicated by a distance between coordinates of the plots indicating the palatants and coordinates of the plots indicating the dogs, respectively;

selecting contributory attributes from the sensory attributes showing a statistically significant correlation with at least one of the palatants;

drawing arrows indicating a respective one of the contributory attributes in the three dimensional map, based on the sensory analysis score; and determining a coordinate of a linking optimum (LO) in the three-dimensional map such that a total of distances between the coordinate of the LO and each of the coordinates of the plots indicating the dogs is minimized, wherein the human tastes only the palatants in the method.

9. The method of claim 8, wherein the plurality of dogs is a plurality of small breed dogs.

10. The method of claim 8, wherein the plurality of dogs is a plurality of beagle dogs.

11. The method of claim 8, wherein the feeding comprises feeding each of the plurality of dogs a pet food not comprising a palatant and pet foods comprising each of the palatants.

12. A method of producing an additive for a pet food, comprising:

selecting a plurality of palatants, where the plurality of palatants includes a roast flavor type hydrolyzed soybean protein, a beer yeast extract, a meat-like flavor material, a hydrolyzed soybean protein, a torula yeast extract, a beef extract, a dried bonito extract, and a cheese paste;

determining a plurality of sensory attributes indicating taste, aroma, and flavor, where the sensory attributes indicating taste consist of sour taste, bitter taste, salty taste, sweet taste, umami taste, mildness, taste intensity, and taste persistence, the sensory attributes indicating aroma consist of sour aroma, fermentation aroma, roast aroma, sweet aroma, fishy aroma, and sulfurous aroma, and the sensory attributes indicating flavor consist of soy sauce-roasted flavor, ocean and dried fish flavor, animal-like flavor, and sour flavor;

performing a sensory analysis of the palatants on a human such that the human tastes each of the palatants and scores an intensity of each of the sensory attributes as a sensory analysis score for each of the palatants;

feeding each of the palatants to a plurality of dogs such that a preference test is performed on the dogs;

generating a three-dimensional map including plots indicating the dogs and plots indicating the palatants based on results of the preference test, such that each dogs' preference on each of the palatants is indicated by a distance between coordinates of the plots indicating the palatants and coordinates of the plots indicating the dogs, respectively;

selecting contributory attributes from the sensory attributes showing a statistically significant correlation with at least one of the palatants;

drawing arrows indicating a respective one of the contributory attributes in the three-dimensional map, based on the sensory analysis score;

determining a coordinate of a linking optimum (LO) in the three-dimensional map such that a total of distances between the coordinate of the LO and each of the coordinates of the plots indicating the dogs is minimized;

calculating an optimal score for each of the contributory attributes by regressing the coordinate of the LO to coordinates of plots indicating each of the palatants;

comparing a difference between the sensory analysis score for each of the palatants and the optimal score for each of the contributory attributes; and mixing the plurality of palatants such that the difference between the sensory analysis score and the optimal score is minimized, wherein the human tastes only the palatants in the method.

* * * * *